(12) United States Patent
Malencheck

(10) Patent No.: US 6,210,374 B1
(45) Date of Patent: Apr. 3, 2001

(54) NEEDLE PROTECTIVE SHEATH DEVICE

(76) Inventor: Robert Malencheck, 279 Sunnymead Rd., Somerville, NJ (US) 08876

( * ) Notice: Subject to any disclaimer, the term of this patent is extended or adjusted under 35 U.S.C. 154(b) by 0 days.

(21) Appl. No.: 09/553,568

(22) Filed: Apr. 20, 2000

(51) Int. Cl.[7] .................................................. A61M 5/00
(52) U.S. Cl. ........................ 604/192; 604/110; 604/198
(58) Field of Search .................................... 604/192, 110, 604/187, 198, 263

(56) References Cited

U.S. PATENT DOCUMENTS

| | | | | |
|---|---|---|---|---|
| 4,915,702 | * | 4/1990 | Haber | 604/198 |
| 5,067,490 | * | 11/1991 | Haber | 604/110 |
| 5,437,639 | * | 8/1995 | Malenchek | 604/198 X |

* cited by examiner

Primary Examiner—John D. Yasko
(74) Attorney, Agent, or Firm—Omri M. Behr, Esq.

(57) ABSTRACT

An inner cylindrical member has a first pair of locking projections on opposite sides of the member at a proximal end and has an extension to which a syringe needle is secured. A second pair of resilient locking projections are spaced from the first pair forming an axially extending locking recess there between at the proximal end. The resilient projections depress to a release position. A pair of finger gripping tabs protrude from the distal end. An outer cylindrical member receives the inner member in its bore. The outer member has an extension which receives the inner member extension and which extensions have mating detents for releasably securing the members in a needle extended use position with the members juxtaposed in nested concentric relation. The outer member at a distal end has projections which mate in the locking recesses at the proximal end to lock the outer member in an extended needle protective position. The resilient locking projections may be depressed to release the locked outer member so it can be displaced to the nested relation of the needle extended position in those cases where the syringe is supplied in the needle protected state of the members. After use, the outer member can be returned to the locked needle protected state.

17 Claims, 4 Drawing Sheets

NEEDLE PROTECTIVE SHEATH DEVICE

This invention relates to needle protective sheath devices, more particularly, protective devices used to protect hypodermic and blood collecting needles.

Of interest is my granted U.S. Pat. No. 5,437,639.

Needle protective sheath devices are in wide use. They typically comprise inner and outer cylindrical members with mating locking ribs and grooves and similar locking devices. The locking ribs and grooves temporarily lock the outer protective sheath in a first mode wherein the needle is exposed and projects from the protective device. This locking position is to preclude the members from accidentally engaging their locking devices in a permanent needle protective locking position prior to use of the needle. The device may be of the type for receiving a plunger in a syringe in a hypodermic application or a vacuum cartridge having a septum which is penetrated by a needle portion inside the bore of a receiving cylinder in a blood collecting application. A blood collecting needle portion projects beyond the cylinder. When its use is completed the outer cylinder member is axially displaced from an overlying position with the inner member to a position cantilevered from the inner member and locked into a needle protective position.

The problem recognized by the present invention is that the prior art devices tend to be permanently locked in the needle use mode which is intended to be temporary. This is because the locking means for the temporary mode tend to be similar in construction as the locking means for the permanent needle protective mode. Therefore, it sometimes may be relatively difficult to disengage the inner and outer cylinder members for placement into the needle protective mode.

However, my above mentioned U.S. patent recognizes this problem and provides a solution thereto. Subsequently, this solution was found to be not completely satisfactory. The present invention addresses these issues and provides an improvement to the device disclosed in my aforementioned patent.

In accordance with an embodiment of the present invention, a needle protective sheath device comprises a first cylindrical member having a first cylindrical cavity defining a longitudinal axis, the member having proximal and distal ends, the member having first and second openings on and extending radially transverse the axis in communication with the cavity on the respective distal and proximal ends, the second opening on the proximal end being restricted in transverse dimension with respect to the first opening on the distal end, the member including needle receiving means at the proximal end opening for securing a needle thereto in communication with the cavity, the secured needle for extending axially beyond the first member proximal end, the member including finger gripping means on the distal end.

A first locking means is on the first cylindrical member outer surface external the cavity on at least one of two opposing member sides adjacent to the proximal end and a second locking means is on the first member outer surface external the cavity adjacent to the proximal end spaced from the first locking means between the first locking means and the distal end forming an axially extending locking recess with the first locking means on the at least one of two opposing sides, the second locking means having a first quiescent locking position forming the recess and a second release position.

A second cylindrical member has a second cylindrical cavity defining a second longitudinal axis, the second member having proximal and distal ends, the second member having third and fourth openings on and extending radially transverse the second axis in communication with the second cavity at the respective distal and proximal ends, the fourth opening on the proximal end being restricted in transverse dimension with respect to the third opening on the distal end, the second cavity for axially receiving the first member through the third opening with the first and second members in nested concentric relation in a first axial relative position with the members overlying one another with their respective proximal and distal ends adjacent to each other and in a second axially extended position wherein the second member distal end is adjacent to the first member proximal end so the second member proximal end extends beyond the first member for protecting the extended needle.

Third locking means are on the second member at the second member distal end for selectively engaging and locking to the first and second locking means in the locking recess in the second extended position, the second locking means being disengaged from the third locking means in the release position for placing the first and second members in the first axial position.

In one embodiment, the at least one first and second locking means are on opposing sides of the first member and the third locking means is on opposing sides of the second member.

In a further embodiment, the second member includes a plurality of ribs for maintaining the first member substantially concentric with the second member as the members displace axially relative to each other.

In a further embodiment, the first and second locking means are axially spaced locking projections extending radially outwardly from the first member outer surface and the third locking means comprises a radially inwardly extending locking projection.

In a further embodiment, the first and third locking means locking projections are secured in relative fixed position to the respective first and second members and the second locking means projection comprises a resilient pawl for selectively being placed in the release position by radially depressing the pawl radially inwardly of the first member.

IN THE DRAWING

FIG. 5a is sectional plan view of the member of FIG. 5 taken along lines 5a—5a;

Figure 1:
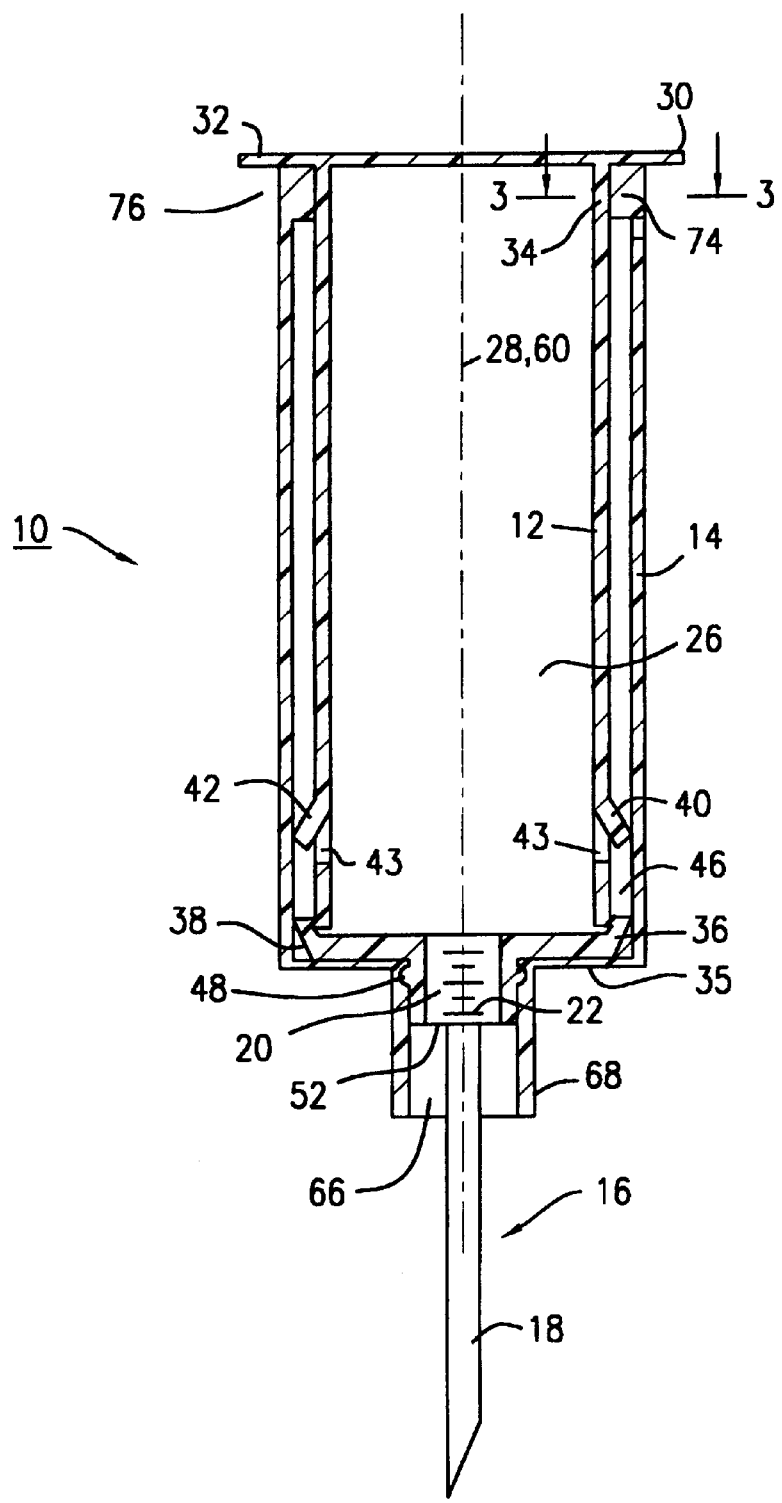
FIG. 1 is a side elevation sectional view of a hypodermic needle device in a needle use mode according to one embodiment of the present invention.

In FIG. 1, needle protective sheath device 10 comprises an inner cylindrical thermoplastic molded member 12 and an outer cylindrical thermoplastic molded member 14. The members are preferable thermoplastic, but could be other materials. In this embodiment the device is employed as a hypodermic syringe as commonly employed in this field, but could be used in a blood collecting implementation as shown in my aforementioned U.S. patent if desired. A needle assembly 16 is attached to the inner member 12.

The needle assembly 16 comprises a hollow needle 18 secured to a thermoplastic connector 20. The connector 20 (FIG. 5) has threads 22. The needle 18 extends beyond the connector 20. A protective cover (not shown) normally extends over the needle 18 when not in use.

Figure 5:
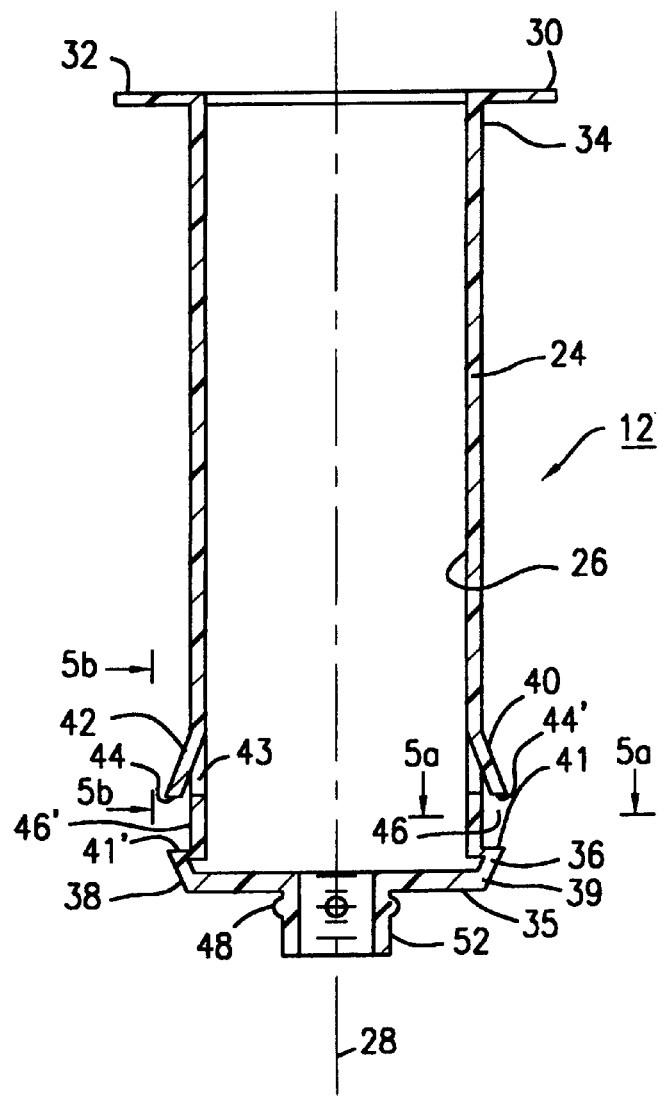
FIG. 5 is a side elevation sectional view of a first cylindrical hollow member of the device of FIG. 1.
Figure 5B:
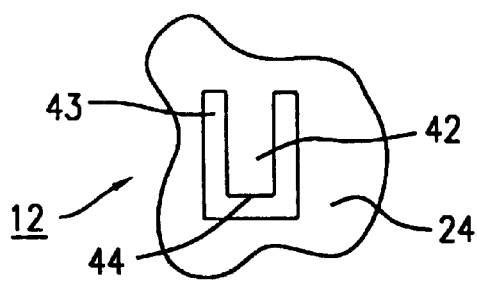
FIG. 5b is fragmented side elevation view of the member of FIG. 5 taken along lines 5b—5b.
Figure 5A:
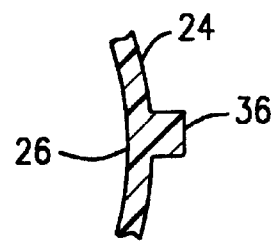

Inner member 12, FIG. 5, comprises a circular cylindrical sleeve 24 having a bore 26 extending along and concentric with longitudinal axis 28. The sleeve 24 has outwardly radially extending finger gripping tabs 30 and 32 at distal end 34 relative to the needle 18 which is at the proximal end 35. A pair of like radially outwardly extending aligned projections 36 and 38, FIGS. 5 and 5a, project from the outer periphery surface of the sleeve 24 in a region adjacent to the proximal end 35. While two projections are shown more or fewer may be provided in the alternative. The projections 36 and 38 may have any desired angular extent about axis 28 according to a given implementation. Representative projection 36 includes an inclined wall 39 forming a planar locking shoulder 41 normal to the outer surface of the member 12 and to the axis 28.

Figure 4:
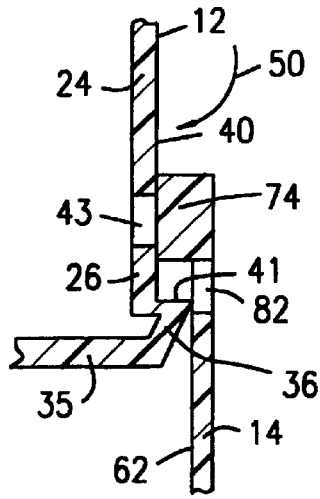
FIG. 4 is a sectional fragmented elevation view of the device of the present invention showing the release position of the releasable locking element.

A pair of like resilient detent projections 40 and 42 which serve as locking pawls extend radially outwardly from the outer periphery surface of the sleeve 24. Representative projection 42, FIG. 5b, comprises a lever which is resiliently hinged to the wall of sleeve 24 by reason of the fact it is a thin sheet of thermoplastic material and has a relative narrow width. Projection 42 overlies opening 43 in the member 12 wall. The projection thus bends in response to a normal radially inwardly directed force thereon, direction 50, FIG. 4.

The projection 42 when depressed enters opening 43 in the member 12 wall, is recessed therein, and the outer surface of the projection 42 becomes flush with the outer surface of the member 12 outer surface. The projection 42 has an edge 44 which forms a shoulder that is generally normal to the outer surface of the member 12 in the quiescent position of the projection 42. However, the orientation of this shoulder surface is not important. As long as the edge 44 is spaced from the plane of the surface of the sleeve 24 of member 12, it forms a locking shoulder in cooperation with shoulder 41' of projection 38. The projections 36, 40, and 38, 42, FIG. 5, respectively form axially extending locking recesses 46, 46'. The projections 40 and 42 when depressed are placed in a release position. The projections 40 and 42 are inclined radially away from the axis 28 as the projections extend toward the proximal end 35.

The proximal end 35 of the member 12 has a reduced cross section area extension 52 having a threaded opening 54. The threads 56 of the opening receives the threads 22 of the needle 18 connector 20 for connection to the proximal end of the member 12. The needle 18 bore is in communication with the bore of sleeve 24. Extension 52 has a plurality of outwardly extending detent bumps 48.

Figure 7:
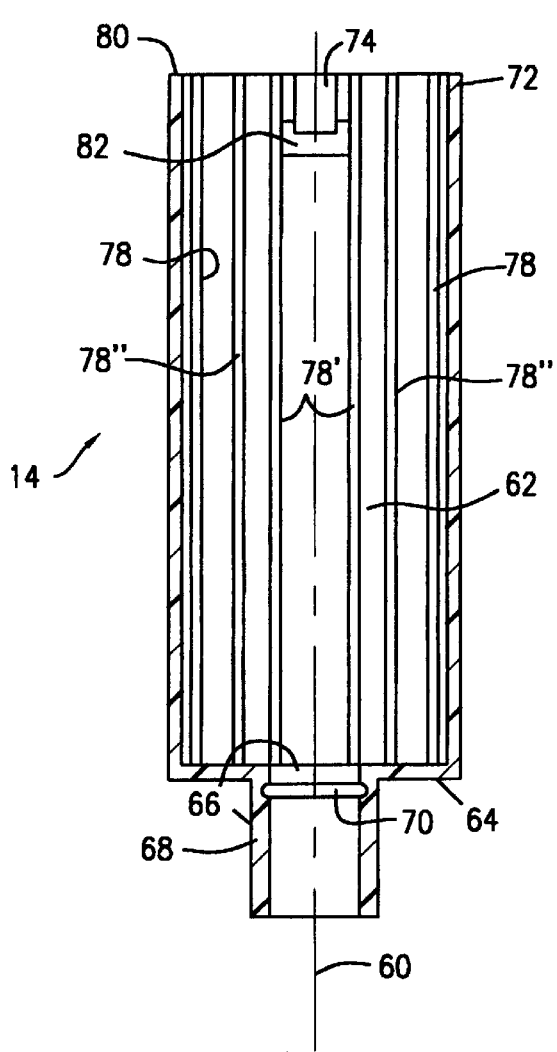
FIG. 7 is a side elevation sectional view of the member of FIG. 6 taken along lines 7—7.
Figure 8:
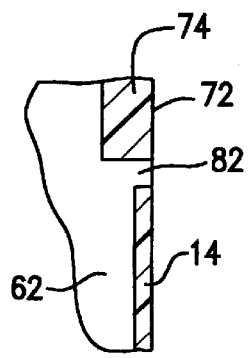
FIG. 8 is a sectional fragmented elevational view of the member of FIG. 7 showing the surface projection and the through opening thereof.

The outer member 14, FIG. 7, is a hollow cylindrical sleeve that has a bore 62 extending along axis 60. The proximal end 64 of the member 14 terminates in a reduced diameter opening 66 in extension 68 for receiving extension 52 (FIG. 1) of member 12. The bore 62 terminates open at the distal end 72. Extension 68 has an inner annular groove 70 for receiving the outwardly extending bumps 48 on the inner member extension 52. These surface features releasably axially secure the inner member detent fashion to the outer member with the inner and outer member proximal ends (and distal ends) juxtaposed as in FIG. 1.

Figure 6:
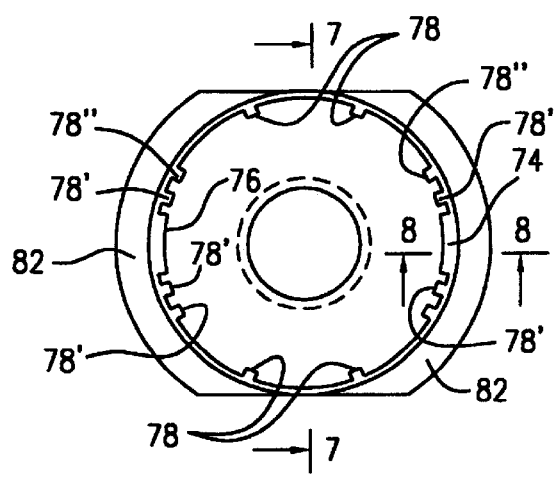
FIG. 6 is a side elevation sectional view of the second cylindrical hollow member of the device of FIG. 1.

The outer member 14 has a pair of like radially inwardly extending like projections 74, 76 at the distal end 72 of the bore 62. The projections 74, 76 are on diametrically opposite sides of the bore 62. An annular array of axially extending ribs 78 of like transverse widths and lengths extend radially inwardly from the inner surface of the member 14 in bore 62. Ribs 78' of like dimensions as ribs 78 are on each side of and spaced somewhat from the projections 74, 76. Another set of ribs 78" are adjacent to the ribs 78'. The ribs 78 are more widely symmetrically spaced apart and from the ribs 78". The ribs are symmetrically spaced in regard to the projections 74 and 76. The ribs have a depth that is about the same as the depth of the projections 74 and 76 and which depth is about the same as that of projections 36 and 38 on the inner member 12, FIGS. 1 and 5. A pair of finger engaging tabs, FIG. 6, extend from the member 14 at proximal end 64, FIG. 7.

Figure 2:
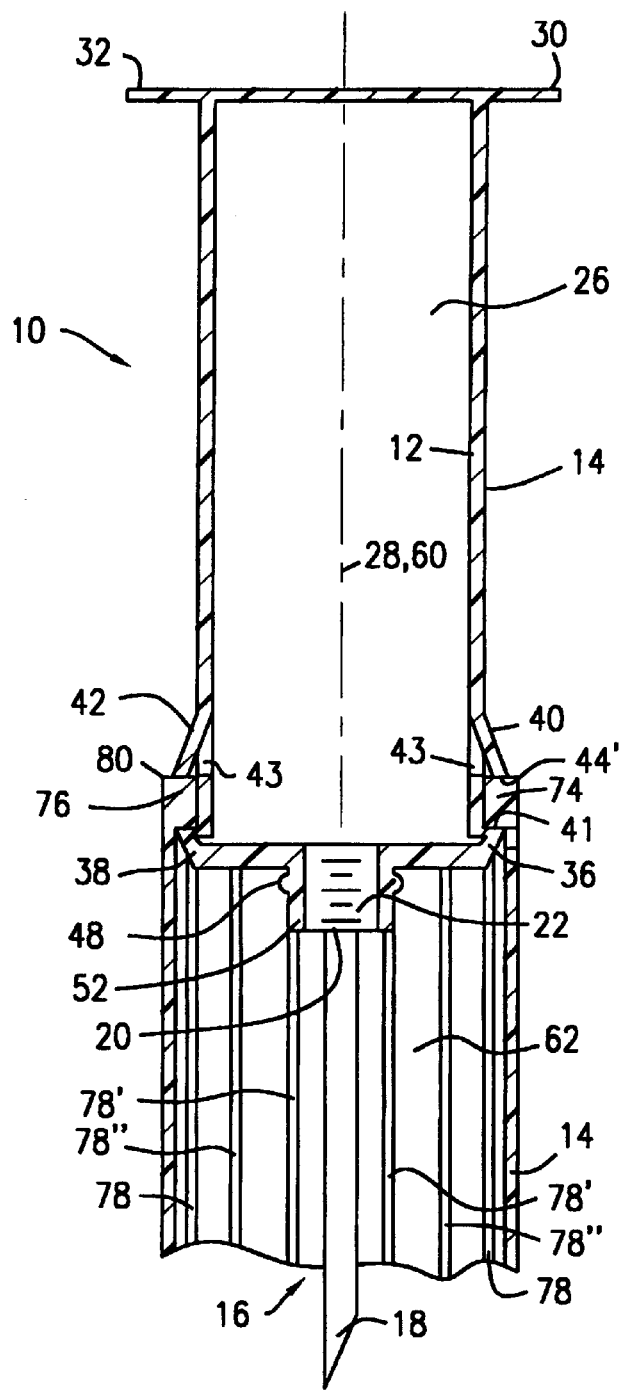
FIG. 2 is a side elevation fragmented sectional view similar to that of FIG. 1 in which the locking means are engaged in a needle protective position.
Figure 3:
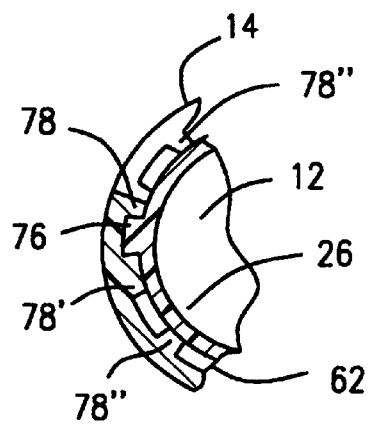
FIG. 3 is a sectional fragmented view of the device of FIG. 1 taken along lines 3—3.

The projections 74, 76 terminate at an end remote from the member 14 top edge 80 at a through opening 82 in the member 14. The projections 74, 76 are rectangular in plan view and have an axial extent along axis 60 which is slightly less than the axial extent of recess 43 of the inner member between the locking projections 36, 40 and 38, 42, FIG. 3. The projections 74, 76 are somewhat narrower in transverse width than the spacing between the ribs 78', FIG. 7. As shown in FIG. 2, the locking projections 36, 40 and 38, 42, FIG. 1, axially lock the respective projections 74 and 76 via the shoulders 41, 41' and projections 40 and 42 edges 44, 44'.

The projections 36 and 38 are fixed to project permanently from the inner member outer surface and the projections 74, 76 are permanently fixed to project radially inwardly from the inner surface of the member 14. As a result, the inner member as it slides axially inside the outer member, may tilt relative to the axes 28, 60 unless otherwise provided for. The ribs 798, 78' and 78" serve this function by maintaining the inner member 12 concentric with the outer member 14 precluding tilting and binding of the two members during relative axial displacement. The ribs 78', FIGS. 6 and 7, form a channel in which the projections 36 and 38 displace as the members displace. The ribs thus lock the members from relative rotation about the axes 28, 60. This keeps the projections 36, 40, and 38, 42 of the inner member 12 axially aligned with projections 74 and 76 of the outer member 14.

In operation, in FIG. 1, the needle assembly 16 is assembled to the inner member 12 extension 52 via connector 20. At this time the outer member 14 is releasably secured to the inner member as shown with the distal ends of the inner and outer members overlying one another and with the proximal ends overlying one another. The securing occurs with the detent bumps 48, FIG. 1, engaged with groove 70 in the outer member 14 extension 68, FIG. 7. The cap or cover (not shown) is removed from the needle 18 and the syringe device is used in the normal manner.

After use, the operator grasps the outer and inner members and pulls the inner and outer members apart in the axial directions. The members are displaced until the locking projections 40 and 42 exit the bore 62, FIG. 2. The projections 40, 42 are depressed by projections 74 and 76 as the projections 40, 42 enter and engage the locking recesses 46. When the projections 74 and 76 are fully engaged with the locking recesses 46 the projections 40 and 42 resiliently snap back to their quiescent position as shown in FIG. 2. The projections 40, 36 and 42, 38 axially lock the locking projections 74, 76 respectively in the needle protective position of FIG. 2.

In the alternative, the device may be packaged as in FIG. 2, with the needle protected by the outer member 14. To use the needle, the projections 40 and 42, FIG. 2, which are external the bore of outer member 14, are depressed, direction 50, FIG. 4, and the outer member is slid out of the locking recesses 46. The locking projections 74 and 76 ride over the projections 40 and 42 keeping them depressed. The outer member is now free to be displaced to the position of FIG. 1 with the needle 18 exposed for use. When the needle has been used, the members 12 and 14 are then returned to the needle safety position of FIG. 2.

While certain embodiments have been described for purposes of illustration, modifications may be made by one of ordinary skill. It is intended that the detailed description be illustrative and not limiting. The scope of the invention is as defined in the appended claims. For example, the number of ribs, projections, their spacing, shape and location may be varied according to a given implementation. The ribs may be replaced by spaced projections which perform the same function. More or fewer ribs may be utilized. While the ribs provide stability to the inner member relative to the outer member during displacement, such ribs may be optional to the extent only that structure is provided to maintain axial alignment of the various projections and locking recesses. Detents may be provided which perform the desired functions but which have different structures and shapes such as resilient material in the form of bumps rather than levers and so on.

What is claimed is:

1. A needle protective sheath device comprising:

a first cylindrical member having a first cylindrical cavity defining a longitudinal axis, said member having proximal and distal ends, said member having first and second openings on and extending radially transverse the axis in communication with the cavity on the respective distal and proximal ends, the second opening on the proximal end being restricted in transverse dimension with respect to the first opening on the distal end, the member including needle receiving means at the proximal end opening for securing a needle thereto in communication with the cavity, the secured needle for extending axially beyond the first member proximal end, the member including finger gripping means on the distal end;

first locking means on the first cylindrical member outer surface external the cavity on at least one of two opposing member sides adjacent to said proximal end;

second locking means on the first member outer surface external the cavity adjacent to the proximal end spaced from said first locking means between said first locking means and the distal end forming an axially extending locking recess with said first locking means on the at least one of two opposing sides, said second locking means having a first quiescent locking position forming the recess and a second release position;

a second cylindrical member having a second cylindrical cavity defining a second longitudinal axis, said second member having proximal and distal ends, said second member having third and fourth openings on and extending radially transverse the second axis in communication with the second cavity at the respective distal and proximal ends, the fourth opening on the proximal end being restricted in transverse dimension with respect to the third opening on the distal end, said second cavity for axially receiving the first member through the third opening with the first and second members in nested concentric relation in a first axial relative position with the members overlying one another with their respective proximal and distal ends adjacent to each other and in a second axially extended position wherein the second member distal end is adjacent to the first member proximal end so the second member proximal end extends beyond the first member for protecting the extended needle; and third locking means on the second member at the second member distal end for selectively engaging and locking to the first and second locking means in said locking recess in said second extended position, the second locking means being disengaged from the third locking means in the release position for placing the first and second members in the first axial position.

2. The device of claim 1 wherein the at least one first and second locking means are on opposing sides of the first member and the third locking means is on opposing sides of the second member.

3. The device of claim 1 wherein the second member includes a plurality of ribs for maintaining the first member substantially concentric with the second member as the members displace axially relative to each other.

4. The device of claim 1 wherein the first and second locking means axially spaced locking projections extending radially outwardly from the first member outer surface and the third locking means comprises a radially inwardly extending locking projection.

5. The device of claim 4 wherein the first and third locking means locking projections are secured in relative fixed position to the respective first and second members and the second locking means projection comprises a resilient pawl for selectively being placed in the release position by radially depressing the pawl radially inwardly of the first member.

6. The device of claim 1 further including a hollow third cylindrical member extending from second member proximal end forming a third axially extending cavity; said needle securing means for engagement in said third cavity with the members in the first axial position, said needle securing means and third cylindrical member including cooperating detent means for releasably securing the first and second members in the first axial position.

7. The device of claim 6 wherein said detent means comprises a radially extending projection on one of said third member and needle securing means and a recess on the other of said third member and needle securing means for receiving the radially extending projection.

8. The device of claim 3 wherein the first locking means comprises a first projection extending radially outwardly from the outer surface of the first member and the third locking means comprises a second projection extending radially inwardly from the second member into the second cavity, the ribs extending radially inwardly from the second member into the second cavity for engaging the outer surface of the first member and for forming a radially inwardly facing channel for receiving the first locking means.

9. The device of claim 1 wherein the second locking means is a resiliently mounted lever forming a ramp, the ramp for slidably engaging the third locking means for placing the second locking means temporarily in the release position to permit the third locking means to be locked as the first and second members are moved axially from the first axial needle extended position to the second axial needle protected position.

10. The device of claim 1 wherein the second locking means comprises a resilient element which is adapted to engage the third locking means for temporarily placing the second locking means in the release position as the third locking means engages said recess, the second locking means resiliently automatically returning to the quiescent locking position upon the engagement of the third locking means with said recess.

11. The device of claim 1 wherein the second and fourth openings are of restricted transverse dimension relative to the first and third openings, respectively, such that the first member can not pass through the fourth opening.

12. The device of claim 1 wherein the first and second locking means are projections having locking shoulders extending substantially normal to the outer surface of the first member and the third locking means comprises a projection with first and second shoulders which abut and lock to the respective first and second locking means shoulders.

13. The device of claim 1 wherein the second locking means is external the second member when the members are in the second axial extended position so that the second locking means is exposed to the ambient atmosphere for selective manual engagement to place the second locking means in the release position.

14. The device of claim 3 including a plurality of said first, second and third locking means and ribs circumferentially spaced about the respective first and second members.

15. A needle protective sheath device comprising:

a first cylindrical member having an axially extending bore extending therethrough and terminating at distal and proximal end edges of the member, first locking means on an outer surface of the first member adjacent to the distal end;

second locking means having a lock position and a manually operated release position and located on the outer surface of the first member axially spaced from the first locking means forming an axially extending locking recess; and a second cylindrical member having an axially extending bore extending therethrough and terminating at distal and proximal member ends for receiving the first member therein in nested concentric relation, said second member having third locking means at the distal end thereof releasably engaged with the first locking means with said members overlying each other in said nested relation in a first relative locked position, said third locking means being released from engagement with the first locking means upon placement of the second locking means in the release position and for locking engagement with the first and second locking means in a second relative position in the locking recess wherein the second member extends cantilevered from the first member in a needle protective position.

16. The device of claim 15 wherein the second member has an annular wall and a plurality of axially extending ribs extending radially inwardly from the wall into the bore thereof and forming an axially extending channel, the first member first and second locking means being engaged with said channel.

17. The device of claim 16 wherein the first and second locking means are projections extending from the peripheral outer surface of the first member forming said locking recess and the third locking means is a projection extending radially inwardly for locking engagement in said recess.

* * * * *